(12) United States Patent
Schmidt et al.

(10) Patent No.: US 6,221,808 B1
(45) Date of Patent: Apr. 24, 2001

(54) METHOD FOR CONTROLLING PARASITIC FUNGI IN CULTIVATED PLANTS

(75) Inventors: Ralf-Michael Schmidt, Neustadt; Hubert Sauter, Mannheim; Eberhard Ammermann, Heppenheim; Gisela Lorenz, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/284,413

(22) PCT Filed: Oct. 8, 1997

(86) PCT No.: PCT/EP97/05534

§ 371 Date: Apr. 14, 1999

§ 102(e) Date: Apr. 14, 1999

(87) PCT Pub. No.: WO98/17115

PCT Pub. Date: Apr. 30, 1998

(30) Foreign Application Priority Data

Oct. 17, 1996 (DE) .............................................. 196 42 880

(51) Int. Cl.$^7$ ...................................................... A01N 63/00
(52) U.S. Cl. ................................................................ 504/117
(58) Field of Search ................................. 504/116; 50/117

(56) References Cited

U.S. PATENT DOCUMENTS 5,436,248 * 7/1995 Zeun et al. ........................... 514/269

FOREIGN PATENT DOCUMENTS

9710716 * 3/1997 (WO) .
9711606 * 4/1997 (WO) .

* cited by examiner

*Primary Examiner*—Jose' G. Dees
*Assistant Examiner*—Alton Pryor
(74) *Attorney, Agent, or Firm*—Keil & Weinkauf

(57) ABSTRACT

A method for controlling harmful fungi in crop plants having modified pathogen resistance to certain harmful fungi, where the crop plant is treated with an active compound from the class of the strobilurins.

17 Claims, No Drawings

METHOD FOR CONTROLLING PARASITIC FUNGI IN CULTIVATED PLANTS

This appln is a 371 of PCT/EP97/05534 filed Oct. 8, 1997.

The present invention relates to a process for controlling harmful fungi in crop plants having modified pathogen resistance against, for example, other harmful fungi.

Methods for controlling harmful fungi in crop plants by using fungicidally active compounds are known per se and are disclosed in the literature.

Also known are crop plants whose pathogen resistance to certain harmful fungi which have a particularly adverse effect on the respective crop plant is modified or increased as compared to the natural level. This may be achieved, for example, by selective breeding or by genetic engineering in that certain DNA sequences which cause increased pathogen resistance when they are functionally expressed in the plant are introduced into the crop plant.

However, owing to the large number of damage-causing mechanisms of harmful fungi, it is often only possible to increase the resistance to a small group of harmful fungi. In addition, plants which are modified in this way often have other disadvantages, for example a lower harvest yield, a higher susceptibility to other harmful fungi, etc.

It is an object of the present invention to provide a method for controlling harmful fungi which allows the control of a wide range of harmful fungi without adversely affecting the yield characteristics of the plants.

We have found that this object is achieved by the method mentioned at the outset, wherein crop plants having modified pathogen resistance to harmful fungi are treated with an active compound of the formula I (IA or IB).

Active compounds of the formula IA or IB are known per se and referred to in the literature as the class of the "strobilurins", in some instances also as "β-methoxyacrylates" (cf. H. Sauter et al., "Mitochondrail [sic] respiration as a target for antifungals: lessons from research in strobilurins" in "Antifungal agents—Discovery and mode of action", G. K. Dixon, L. G. Copping and D. W. Holloman (Editors), BIOS Scientific Publishers, Oxford 1995, p. 175 ff.).

In particular, representatives of active compounds of the formula I (or IA and IB) having fungicidal and in part also bioregulatory activity are described in the following publications:

EP-A 178 826, EP-A 203 606, EP-A 203 608, EP-A 206 523, EP-A 212 859, EP-A 226 917, EP-A 226 974, EP-A 242 070, EP-A 242 081, EP-A 243 012, EP-A 243 014, EP-A 251 082, EP-A 253 213, EP-A 254 426, EP-A 256 667, EP-A 260 794, EP-A 260 832, EP-A 267 734, EP-A 273 572, EP-A 274 825, EP-A 278 595, EP-A 280 185, EP-A 291 196, EP-A 299 694, EP-A 307 101, EP-A 307 103, EP-A 310 954, EP-A 312 221, EP-A 312 243, EP-A 329 011, EP-A 331 966, EP-A 335 519, EP-A 336 211, EP-A 337 211, EP-A 341 845, EP-A 350 691, EP-A 354 571, EP-A 363 818, EP-A 370 629, EP-A 373 775, EP-A 374 811, EP-A 378 308, EP-A 378 755, EP-A 379 098, EP-A 382 375, EP-A 383 117, EP-A 384 211, EP-A 385 224, EP-A 385 357, EP-A 386 561, EP-A 386 681, EP-A 389 901, EP-A 391 451, EP-A 393 428, EP-A 393 861, EP-A 398 692, EP-A 400 417, EP-A 402 246, EP-A 405 782, EP-A 407 873, EP-A 409 369, EP-A 414 153, EP-A 416 746, EP-A 420 091, EP-A 422 597, EP-A 426 460, EP-A 429 968, EP-A 430 471, EP-A 433 233, EP-A 433 899, EP-A 439 785, EP-A 459 285, EP-A 460 575, EP-A 463 488, EP-A 463 513, EP-A 464 381, EP-A 468 684, EP-A 468 695, EP-A 468 775, EP-A 471 261, EP-A 472 224, EP-A 472 300, EP-A 474 042, EP-A 475 158, EP-A 477 631, EP-A 480 795, EP-A 483 851, EP-A 483 985, EP-A 487 409, EP-A 493 711, EP-A 498 188, EP-A 498 396, EP-A 499 823, EP-A 503 436, EP-A 508 901, EP-A 509 857, EP-A 513 580, EP-A 515 901, EP-A 517 301, EP-A 528 245, EP-A 532 022, EP-A 532 126, EP-A 532 127, EP-A 535 980, EP-A 538 097, EP-A 544 587, EP-A 546 387, EP-A 548 650, EP-A 564 928, EP-A 566 455, EP-A 567 828, EP-A 571 326, EP-A 579 071, EP-A 579 124, EP-A 579 908, EP-A 581 095, EP-A 582 902, EP-A 582 925, EP-A 583 806, EP-A 584 625, EP-A 585 751, EP-A 590 610, EP-A 596 254, WO-A 90/07,493, WO-A 92/13,830, WO-A 92/18, 487, WO-A 92/18,494, WO-A 92/21,653, WO-A 93/07, 116, WO-A 93/08,180, WO-A 93/08,183, WO-A 93/15, 046, WO-A 93/16,986, WO-A 94/00,436, WO-A 94/05, 626, WO-A 94/08,948, WO-A 94/08,968, WO-A 94/10, 159, WO-A 94/11,334, JP-A 02/121,970, JP-A 04/182, 461, JP-A 05/201,946, U.S. Pat. No. 5,335,283, JP-A 05/255,012, JP-A 05/294,948, JP-A 06/025,133, JP-A 06/025,142, JP-A 06/056,756, FR-A 2 670 781, GB-A 2 210 041, GB-A 2 218 702, GB-A 2 238 308, GB-A 2 249 092, GB-A 2 253 624, GB-A 2 255 092, WO-A 90/10006, WO-A 94/22812, EP-A-627 411, EP-A 647 631, EP-A 741 698, EP-A 738 259, EP-A 741 694, EP-A 673 923.

Suitable for the method according to the invention are generally all active compounds of the formulae IA and IB

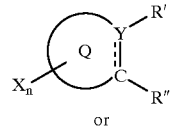

IA or

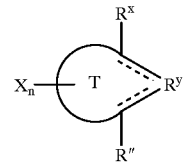

IB described in the publications mentioned at the outset in which R" is one of the following groups:

aryloxy with or without substitution, hetaryloxy with or without substitution, aryloxymethylene with or without substitution, hetaryloxymethylene with or without substitution, arylethenylene with or without substitution, and hetarylethenylene with or without substitution, or a group $R^\alpha R^\beta C=NOCH_2-$ or $R^\gamma ON=CR^\delta CR^\epsilon =NOCH_2$ where the radicals $R^\alpha$, $R^\beta$, $R^\gamma$, $R^\delta$ and $R^\epsilon$ in general and in particular have the meanings described in the following publications:

EP-A 370 629, EP-A 414 153, EP-A 426 460, EP-A 460 575, EP-A 463 488, EP-A 472 300, EP-A 498 188, EP-A 498 396, EP-A 515 901, EP-A 585 751, WO-A 90/07,493, WO-A 92/13,830, WO-A 92/18,487, WO-A 92/18,494, WO-A 93/15,046, WO-A 93/16,986, WO-A 94/08,948, WO-A 94/08,968, JP-A 05/201,946, JP-A 05/255,012, JP-A 05/294,948, JP-A 06/025,133, JP-A 061025,142, EP-A 738 259, EP-A 741 694, EP-A 738 259 and WO-A 95/21154, particularly preferred radicals "aryloxy with or without substitution, hetaryloxy with or without substitution" in general and in particular have the meanings described in the following publications:

EP-A 178 826, EP-A 242 070, EP-A 242 081, EP-A 253 213, EP-A 254 426, EP-A 256 667, EP-A 260 794, EP-A 280 185, EP-A 307 103, EP-A 341 845, EP-A 382 375, EP-A 393 861, EP-A 398 692, EP-A 405 782, EP-A 430 471, EP-A 468 684, EP-A 468 695, EP-A 477 631, EP-A 483 985, EP-A 498 188, EP-A 513 580, EP-A 515 901, WO-A 93115,046, WO-A 94110,159, GB-A 2 253 624 and JP-A 041182,461;

particularly preferred radicals "aryloxymethylene with or without substitution, hetaryloxymethylene with or without substitution" in general and in particular have the meanings described in the following publications:

EP-A 178 826, EP-A 226 917, EP-A 253 213, EP-A 254 426, EP-A 278 595, EP-A 280 185, EP-A 299 694, EP-A 335 519, EP-A 350 691, EP-A 363 818, EP-A 373 775, EP-A 378 308, EP-A 385 224, EP-A 386 561, EP-A 398 692, EP-A 400 417, EP-A 407 873, EP-A 472 224, EP-A 477 631, EP-A 498 188, EP-A 498 396, EP-A 513 580, EP-A 515 901, EP-A 579 124, WO-A 93/08,180, WO-A 93/15,046, WO-A 94/00,436, JP-A 04/182,461, WO-A 90/10006, EP-A 673 923 and EP-A 758 322;

particularly preferred radicals "arylethenylene, with or without substitution, hetarylethenylene with or without substitution" in general and in particular have the meanings described in the following publications:

EP-A 178 826, EP-A 203 606, EP-A 253 213, EP-A 254 426, EP-A 280 185, EP-A 378 755, EP-A 398 692, EP-A 402 246, EP-A 474 042, EP-A 475 158, EP-A 477 631, EP-A 487 409, EP-A 498 188, EP-A 498 396, EP-A 513 580, EP-A 515 901, EP-A 528 245, EP-A 544 587, WO-A 93/15,046, WO-A 94/11,334 and FR-A 2 670 781 and EP-A 691 332.

Particularly preferred active compounds of the formula IA in which R' is —C[CO$_2$CH$_3$]=CHOCH$_3$ in general and in particular correspond to the compounds described in the following publications:

EP-A 178 826, EP-A 203 606, EP-A 226 917, EP-A 242 070, EP-A 242 081, EP-A 256 667, EP-A 260 794, EP-A 278 595, EP-A 299 694, EP-A 307 103, EP-A 335 519, EP-A 341 845, EP-A 350 691, EP-A 370 629, EP-A 373 775, EP-A 378 308, EP-A 378 755, EP-A 382 375, EP-A 385 224, EP-A 386 561, EP-A 393 861, EP-A 402 246, EP-A 405 782, EP-A 407 873, EP-A 414 153, EP-A 426 460, EP-A 430 471, EP-A 463 488, EP-A 468 695, EP-A 472 224, EP-A 474 042, EP-A 475 158, EP-A 483 985, EP-A 487 409, EP-A 515 901, EP-A 528 245, EP-A 544 587, WO-A 90/07,493, WO-A 92118,487, WO-A 92/18,494, WO-A 93/08,180, WO-A 93116,986, WO-A 94/00,436, WO-A 94/08,948, WO-A 94/08,968, WO-A 94/10,159, WO-A 94111,334, FR-A 2 670 781, JP-A 06/025,133, EP-A 738 259, EP-A 673 923 particularly preferred active compounds of the formula IA where R' is —C[CO$_2$CH$_3$]=NOCH$_3$ in general and in particular correspond to the compounds described in the following publications:

EP-A 253 213, EP-A 254 426, EP-A 299 694, EP-A 363 818, EP-A 378 308, EP-A 385 224, EP-A 386 561, EP-A 400 417, EP-A 407 873, EP-A 460 575, EP-A 463 488, EP-A 468 684, EP-A 472 300, EP-A 515 901, WO-A 94/00,436, WO-A 94/08,948, WO-A 94/10,159, WO-A 94/11,334, JP-A 05/201,946, JP-A 05/255,012, JP-A 05/294,948, EP-A 738 259, EP-A 673 923 particularly preferred active compounds of the formula IA in which R' is —C[CONHCH$_3$]=NOCH$_3$ in general and in particular correspond to the compounds described in the following publications:

EP-A 398 692, EP-A 463 488, EP-A 477 631, EP-A 515 901, EP-A 579 124, EP-A 585 751, WO-A 92/13,830, WO-A 93/08,180, WO-A 94/08,948, WO-A 94/10,159, WO-A 94/11,334, GB-A 2 253 624, JP-A 04/182,461, JP-A 05/201,946, JP-A 05/255,012, JP-A 05/294,948, WO-A 90/10006, EP-A 741 694, EP-A 673 923, EP-A 691 332 and WO-A 95/21154 particularly preferred active compounds of the formula IA in which R' is —C[CO$_2$CH$_3$]=CHCH$_3$ or —C[CO$_2$CH$_3$]=CHCH$_2$CH$_3$ in general and in particular correspond to the compounds described in the following publications:

EP-A 280 185, EP-A 463 488, EP-A 513 580, EP-A 515 901, EP-A 738 259, EP-A 673 923 and EP-A 758 322 particularly preferred active compounds of the formula IA in which R' is —C[COCH$_3$]=NOCH$_3$ or —C[COCH$_2$CH$_3$]=NOCH$_3$ in general and in particular correspond to the compounds described in EP-A 498 188;

particularly preferred active compounds of the formula IA in which R' is —N(OCH$_3$)—CO$_2$CH$_3$, —N(CH$_3$)—CO$_2$CH$_3$ or —N(CH$_2$CH$_3$)—CO$_2$CH$_3$ in general and in particular correspond to the compounds described in the following publications: EP-A 498 396, WO-A 93/15,046, JP-A 06/025, 142 and JP-A 06/056,756;

particularly preferred active compounds of the formula IB in which R is —OC[CO$_2$CH$_3$]=CHOCH$_3$, —OC[CO$_2$CH$_3$]=CHCH$_3$, —OC[CO$_2$CH$_3$]=CHCH$_2$CH$_3$, —SC[CO$_2$CH$_3$]=CHOCH$_3$, —SC[CO$_2$CH$_3$]=CHCH$_3$, —SC[CO$_2$CH$_3$]=CHCH$_2$CH$_3$, —N(CH$_3$)C[CO$_2$CH$_3$]=CHOCH$_3$, —N(CH$_3$)C[CO$_2$CH$_3$]=NOCH$_3$, —CH$_2$C[CO$_2$CH$_3$]=CROCH$_3$, —CH$_2$C[CO$_2$CH$_3$]=NOCH$_3$ or —CH$_2$C[CONHCH$_3$]=NOCH$_3$ in general and in particular correspond to the compounds described in the following publications:

EP-A 212 859, EP-A 331 966, EP-A 383 117, EP-A 384 211, EP-A 389 901, EP-A 409 369, EP-A 464 381, EP-A 471 261, EP-A 503 436, EP-A 546 387, EP-A 548 650, EP-A 579 908 and EP-A 584 625.

Examples of particularly suitable active compounds IA and IB are listed in the tables below.

TABLE 1.1A

Compounds of the formula IA where Q is phenyl, R' is —C(CO$_2$CH$_3$)=CHOCH$_3$, n is 0, R" is (het)aryloxymethylene with or without substitution, where the (het)aryl group with or without substitution has the following meanings:

| No. | (Het)aryl with or without substitution | Literature |
|---|---|---|
| I.1A-1 | 2-CH$_3$—C$_6$H$_4$ | EP-A 226 917 |
| I.1A-2 | 2,5-(CH$_3$)$_2$—C$_6$H$_3$ | EP-A 226 917 |
| I.1A-3 | 2-CH$_3$, 4-C[CH$_3$]=NOCH$_3$—C$_6$H$_3$ | EP-A 386 561 |
| I.1A-4 | 2-CH$_2$CH$_2$CH$_3$, 6-CF$_3$-pyrimidin-4-yl | EP-A 407 873 |

TABLE 1.1B

Compounds of the formula IA where R' is —C(CO$_2$CH$_3$)=CHOCH$_3$, Q is phenyl, n is 0, R" is (het)aryloxy with or without substitution, where the (het)aryl group with or without substitution has the following meanings:

| No. | (Het)aryl with or without substitution | Literature |
|---|---|---|
| I.1B-1 | C$_6$H$_5$ | EP-A 178 826 |
| I.1B-2 | 6-[2-CN—C$_6$H$_4$—O]-pyrimidin-4-yl | EP-A 382 375 |

TABLE 1.1C

Compounds of the formula IA where R' is —C(CO$_2$CH$_3$)=CHOCH$_3$, Q is phenyl, n is 0, R" is (het)arylethenylene with or without substitution, where the (het)aryl group with or without substitution has the following meanings:

| No. | (Het)aryl with or without substitution | Literature |
|---|---|---|
| I.1C-1 | 1-(2,4-Cl$_2$—C$_6$H$_3$), 5-CF$_3$-pyrazol-4-yl | EP-A 528 245 |
| I.1C-2 | 1-(4-Cl—C$_6$H$_4$)-pyrazol-4-yl | EP-A 378 755 |
| I.1C-3 | 3-CF$_3$—C$_6$H$_4$ | EP-A 203 606 |
| I.1C-4 | 3-Cl—C$_6$H$_4$ | EP-A 203 606 |
| I.1C-5 | 4-C$_6$H$_5$—C$_6$H$_4$ | EP-A 203 606 |

TABLE 1.1D

Compounds of the formula IA where Q is phenyl, R' is —C(CO$_2$CH$_3$)=CHOCH$_3$, n is 0, R" is CH$_2$ON=CR$^\alpha$R$^\beta$, where R$^\alpha$ and R$^\beta$ have the following meanings:

| No. | R$^\alpha$ | R$^\beta$ | Literature |
|---|---|---|---|
| I.1D-1 | CH$_3$ | 4-Cl—C$_6$H$_4$ | EP-A 370 629 |
| I.1D-2 | CH$_3$ | 3-CF$_3$—C$_6$H$_4$ | EP-A 370 629 |
| I.1D-3 | CH$_3$ | 4-OCH$_2$CH$_3$-pyrimidin-2-yl | WO-A 92/18,487 |

TABLE 1.1E

Compounds of the formula IA where Q is phenyl, R' is —C(CO$_2$CH$_3$)=CHOCH$_3$, n is 0, R" is CH$_2$ON=CR$^\gamma$CR$^\delta$=NOR$^\epsilon$, where R$^\gamma$, R$^\delta$ and R$^\epsilon$ have the following meanings:

| No. | R$^\gamma$ | R$^\delta$ | R$^\epsilon$ | Literature |
|---|---|---|---|---|
| I.1E-1 | CH$_3$ | CH$_3$ | CH$_3$ | EP-A 738 259 |
| I.1E-2 | CH$_3$ | CH$_3$ | CH$_2$CH$_3$ | EP-A 738 259 |
| I.1E-3 | CH$_3$ | C$_6$H$_5$ | CH$_3$ | EP-A 738 259 |
| I.1E-4 | CH$_3$ | C$_6$H$_5$ | CH$_2$CH$_3$ | EP-A 738 259 |
| I.1E-5 | CH$_3$ | 4-Cl—C$_6$H$_4$ | CH$_3$ | EP-A 738 259 |
| I.1E-6 | CH$_3$ | 4-Cl—C$_6$H$_4$ | CH$_2$CH$_3$ | EP-A 738 259 |

TABLE 1.2A

Compounds of the formula IA where Q is phenyl, R' is —C(CO$_2$CH$_3$)=NOCH$_3$, n is 0, R" is (het)aryloxymethylene with or without substitution, where the (het)aryl group with or without substitution has the following meanings:

| No. | (Het)aryl with or without substitution | Literature |
|---|---|---|
| I.2A-1 | 2-CH$_3$—C$_6$H$_4$ | EP-A 253 213 |
| I.2A-2 | 2,5-(CH$_3$)$_2$—C$_6$H$_3$ | EP-A 400 417 |
| I.2A-3 | 2,4-(CH$_3$)$_2$—C$_6$H$_3$ | EP-A 400 417 |
| I.2A-4 | 2,3,5-(CH$_3$)$_3$—C$_6$H$_2$ | EP-A 400 417 |
| I.2A-5 | 2-Cl, 5-CH$_3$—C$_6$H$_3$ | EP-A 400 417 |
| I.2A-6 | 2-CH$_3$, 4-C[CH$_3$]=NOCH$_3$—C$_6$H$_3$ | EP-A 386 561 |

TABLE 1.2B

Compounds of the formula IA where Q is phenyl, R' is —C(CO$_2$CH$_3$)=NOCH$_3$, n is 0, R" is (het)aryloxy with or without substitution, where the (het)aryl group with or without substitution has the following meanings:

| No. | (Het)aryl with or without substitution | Literature |
|---|---|---|
| I.2B-1 | C$_6$H$_5$ | EP-A 253 213 |
| I.2B-2 | 6-[2-CN—C$_6$H$_4$—O]-pyrimidin-4-yl | EP-A 468 684 |

TABLE 1.2C

Compounds of the formula IA where Q is phenyl, R' is —C(CO$_2$CH$_3$)=NOCH$_3$, n is 0, R" is CH$_2$ON=CR$^\alpha$R$^\beta$, where R$^\alpha$ and R$^\beta$ have the following meanings:

| No. | R$^\alpha$ | R$^\beta$ | Literature |
|---|---|---|---|
| I.2C-1 | CH$_3$ | 4-Cl—C$_6$H$_4$ | EP-A 463 488 |
| I.2C-2 | CH$_3$ | 3-Cl—C$_6$H$_4$ | EP-A 463 488 |
| I.2C-3 | CH$_3$ | 4-CF$_3$—C$_6$H$_4$ | EP-A 463 468 |
| I.2C-4 | CH$_3$ | 3-CF$_3$—C$_6$H$_4$ | EP-A 463 488 |
| I.2C-5 | CH$_3$ | 4-CH$_3$—C$_6$H$_4$ | EP-A 463 488 |
| I.2C-6 | CH$_3$ | 4-OCH$_2$CH$_3$-pyrimidin-2-yl | EP-A 472 300 |
| I.2C-7 | CH$_3$ | 3,5-Cl$_2$—C$_6$H$_3$ | EP-A 463 488 |

TABLE 1.2D

Compounds of the formula IA where Q is phenyl, R' is —C(CO$_2$CH$_3$)=NOCH$_3$, n is 0, R" is CH$_2$ON=CR$^\gamma$CR$^\delta$=NOR$^\epsilon$, where R$^\gamma$, R$^\delta$ and R$^\epsilon$ have the following meanings:

| No. | R$^\gamma$ | R$^\delta$ | R$^\epsilon$ | Literature |
|---|---|---|---|---|
| I.2D-1 | CH$_3$ | CH$_3$ | CH$_3$ | EP-A 738 259 |
| I.2D-2 | CH$_3$ | CH$_3$ | CH$_2$CH$_3$ | EP-A 738 259 |
| I.2D-3 | CH$_3$ | C$_6$H$_5$ | CH$_3$ | EP-A 736 259 |
| I.2D-4 | CH$_3$ | C$_6$H$_5$ | CH$_2$CH$_3$ | EP-A 738 259 |
| I.2D-5 | CH$_3$ | 4-Cl—C$_6$H$_4$ | CH$_3$ | EP-A 736 259 |
| I.2D-6 | CH$_3$ | 4-Cl—C$_6$H$_4$ | CH$_2$CH$_3$ | EP-A 738 259 |

TABLE 1.3A

Compounds of the formula IA where Q is phenyl, R' is —C(CONHCH$_3$)=NOCH$_3$, n is 0, R" is (het)aryloxymethylene with or without substitution, where the (het)aryl group with or without substitution has the following meanings:

| No. | (Het)aryl with or without substitution | Literature |
|---|---|---|
| I.3A-1 | 2-CH$_3$—C$_6$H$_4$ | EP-A 477 631 |
| I.3A-2 | 2,5-(CH$_3$)$_2$—C$_6$H$_3$ | EP-A 477 631 |
| I.3A-3 | 2,4-(CH$_3$)$_2$—C$_6$H$_3$ | EP-A 477 631 |
| I.3A-4 | 2,3,5-(CH$_3$)$_3$—C$_6$H$_2$ | EP-A 477 631 |
| I.3A-5 | 2-CH$_3$, 4-C[CH$_3$]=NOCH$_3$—C$_6$H$_3$ | EP-A 579 124 |
| I.3A-6 | 1-[4-Cl—C$_6$H$_4$]-pyrazol-3-yl | WO-A 90/10006 |
| I.3A-7 | 1-[2,4-Cl$_2$—C$_6$H$_3$]-pyrazol-3-yl | WO-A 90/10006 |

TABLE 1.3B

Compounds of the formula IA where Q is phenyl, R' is —C(CONHCH$_3$)=NOCH$_3$, n is 0, R" is (het)aryloxy with or without substitution, where the (het)aryl group with or without substitution has the following meanings:

| No. | (Het)aryl with or without substitution | Literature |
|---|---|---|
| I.3B-1 | C$_6$H$_5$ | EP-A 398 692 |
| I.3B-2 | 6-[2-CN—C$_6$H$_4$—O]-pyrimidin-4-yl | GB-A 2 253 624 |

TABLE 1.3C

Compounds of the formula IA where Q is phenyl, R' is
—C(CONHCH$_3$) = NOCH$_3$, n is 0, R" is (het)arylethenylene with or without substitution, where the (het)aryl group with or without substitution has the following meaning:

| No. | (Het)aryl with or without substitution | Literature |
| --- | --- | --- |
| I.3C-1 | 1-[2,4-Cl$_2$—C$_6$H$_3$], 5-CF$_3$-pyrazol-4-yl | EP-A 691 332 |

TABLE 1.3D

Compounds of the formula IA where Q is phenyl, R' is
—C(CONHCH$_3$)=NOCH$_3$, n is 0, R" is CH$_2$ON=CR$^\alpha$R$^\beta$, where R$^\alpha$ and R$^\beta$ have the following meanings:

| No. | R$^\alpha$ | R$^\beta$ | Literature |
| --- | --- | --- | --- |
| I.3D-1 | CH$_3$ | 4-Cl—C$_6$H$_4$ | EP-A 463 488 |
| I.3D-2 | CH$_3$ | 3-Cl—C$_6$H$_4$ | EP-A 463 488 |
| I.3D-3 | CH$_3$ | 4-CF$_3$—C$_6$H$_4$ | EP-A 585 751 |
| I.3D-4 | CH$_3$ | 3-CF$_3$—C$_6$H$_4$ | EP-A 585 751 |
| I.3D-5 | CH$_3$ | 4-CH$_3$—C$_6$H$_4$ | EP-A 463 488 |
| I.3D-6 | CH$_3$ | 3,5-Cl$_2$—C$_6$H$_3$ | EP-A 463 488 |
| I.3D-7 | CH$_3$ | 2-OCH$_2$CH$_3$—pyrimidin-2-yl | WO-A 92/13,830 |

TABLE 1.3E

Compounds of the formula IA where Q is phenyl, R' is
—C(CONHCH$_3$)=NOCH$_3$, n is 0, R" is CH$_2$ON=CR$^\gamma$CR$^\delta$=NOR$^\epsilon$, where R$^\gamma$, R$^\delta$ and R$^\epsilon$ have the following meanings:

| No. | R$^\gamma$ | R$^\delta$ | R$^\epsilon$ | Literature |
| --- | --- | --- | --- | --- |
| I.3E-1 | CH$_3$ | CH$_3$ | CH$_3$ | WO-A 95/21154 |
| I.3E-2 | CH$_3$ | CH$_3$ | CH$_2$CH$_3$ | WO-A 95/21154 |
| I.3E-3 | CH$_3$ | C$_6$H$_5$ | CH$_3$ | WO-A 95/21154 |
| I.3E-4 | CH$_3$ | C$_6$H$_5$ | CH$_2$CH$_3$ | WO-A 95/21154 |
| I.3E-5 | CH$_3$ | 4-Cl—C$_6$H$_4$ | CH$_3$ | WO-A 95/21154 |
| I.3E-6 | CH$_3$ | 4-Cl—C$_6$H$_4$ | CH$_2$CH$_3$ | WO-A 95/21154 |

TABLE 1.4A

Compounds of the formula IA where Q is phenyl, R' is
—C(CO$_2$CH$_3$)=CHCH$_3$, n is 0, R" is (het)aryloxymethylene with or without substitution when the het(aryl) group with or without substitution has the following meanings:

| No. | (Het)aryl with or without substitution | Literature |
| --- | --- | --- |
| I.4A-1 | 2-CH$_3$—C$_6$H$_4$ | EP-A 280 185 |
| I.4A-2 | 2,5-(CH$_3$)$_2$—C$_6$H$_3$ | EP-A 513 580 |
| I.4A-3 | 2,4-(CH$_3$)$_2$—C$_6$H$_3$ | EP-A 513 580 |
| I.4A-4 | 2,3,5-(CH$_3$)$_3$—C$_6$H$_2$ | EP-A 513 580 |
| I.4A-5 | 2-Cl, 5-CH$_3$—C$_6$H$_3$ | EP-A 513 580 |
| I.4A-6 | 2-CH$_3$, 4-C[CH$_3$]=NOCH$_3$—C$_6$H$_3$ | EP-A 513 580 |
| I.4A-7 | 1-[4-Cl—C$_6$H$_4$]-pyrazol-3-yl | EP-A 758 322 |

TABLE 1.4B

Compounds of the formula IA where Q is phenyl, R' is
—C(CO$_2$CH$_3$) = CHCH$_3$, n is 0, R" is (het)aryloxy with or without substitution, where the (het)aryl group with or without substitution has the following meaning:

| No. | (Het)aryl with or without substitution | Literature |
| --- | --- | --- |
| I.4B-1 | C$_6$H$_5$ | EP-A 513 580 |

TABLE 1.4C

Compounds of the formula IA where Q is phenyl, R' is
—C(CO$_2$CH$_3$) = CHCH$_3$, n is 0, R" is CH$_2$ON = CR$^\gamma$CR$^\delta$ = NOR$^\epsilon$, where R$^\gamma$, R$^\delta$ and R$^\epsilon$ have the following meanings:

| No. | R$^\gamma$ | R$^\delta$ | R$^\epsilon$ | Literature |
| --- | --- | --- | --- | --- |
| I.4C-1 | CH$_3$ | CH$_3$ | CH$_3$ | EP-A 738 259 |
| I.4C-2 | CH$_3$ | CH$_3$ | CH$_2$CH$_3$ | EP-A 738 259 |
| I.4C-3 | CH$_3$ | C$_6$H$_5$ | CH$_3$ | EP-A 738 259 |
| I.4C-4 | CH$_3$ | C$_6$H$_5$ | CH$_2$CH$_3$ | EP-A 738 259 |
| I.4C-5 | CH$_3$ | 4-Cl—C$_6$H$_4$ | CH$_3$ | EP-A 738 259 |
| I.4C-6 | CH$_3$ | 4-Cl—C$_6$H$_4$ | CH$_2$CH$_3$ | EP-A 73B 259 |

TABLE 1.5A

Compounds of the formula IA where Q is phenyl, R' is
—C(CO$_2$CH$_3$)=CHCH$_2$CH$_3$, n is 0, R" is (het)aryloxymethylene with or without substitution, where the (het)aryl group with or without substitution has the following meanings:

| No. | (Het)aryl with or without substitution | Literature |
| --- | --- | --- |
| I.5A-1 | 2-CH$_3$—C$_6$H$_4$ | EP-A 513 580 |
| I.5A-2 | 2,5-(CH$_3$)$_2$—C$_6$H$_3$ | EP-A 513 580 |
| I.5A-3 | 2,4-(CH$_3$)$_2$—C$_6$H$_3$ | EP-A 513 580 |
| I.5A-4 | 2,3,5-(CH$_3$)$_3$—C$_6$H$_2$ | EP-A 513 580 |
| I.5A-5 | 2-Cl, 5-CH$_3$—C$_6$H$_3$ | EP-A 513 580 |
| I.5A-6 | 2-CH$_3$, 4-C[CH$_3$]=NOCH$_3$—C$_6$H$_3$ | EP-A 513 580 |

TABLE 1.5B

Compounds of the formula IA where Q is phenyl, R' is
—C(CO$_2$CH$_3$) = CHCH$_2$CH$_3$, n is 0, R" is (het)aryloxy with or without substitution, where the (het)aryl group with or without substitution has the following meaning:

| No. | (Het)aryl with or without substitution | Literature |
| --- | --- | --- |
| I.5B-1 | C$_6$H$_5$ | EP-A 513 580 |

TABLE 1.5C

Compounds of the formula IA where Q is phenyl, R' is —C(CO$_2$CH$_3$) = CHCH$_2$CH$_3$, n is 0, R" is CH$_2$ON = CR$^\gamma$CR$^\delta$ = NOR$^\epsilon$, where R$^\gamma$, R$^\delta$ and R$^\epsilon$ have the following meanings:

| No. | R$^\gamma$ | R$^\delta$ | R$^\epsilon$ | Literature |
| --- | --- | --- | --- | --- |
| I.5C-1 | CH$_3$ | CH$_3$ | CH$_3$ | EP-A 738 259 |
| I.5C-2 | CH$_3$ | CH$_3$ | CH$_2$CH$_3$ | EP-A 738 259 |
| I.5C-3 | CH$_3$ | C$_6$H$_5$ | CH$_3$ | EP-A 738 259 |
| I.5C-4 | CH$_3$ | C$_6$H$_5$ | CH$_2$CH$_3$ | EP-A 738 259 |
| I.5C-5 | CH$_3$ | 4-Cl—C$_6$H$_4$ | CH$_3$ | EP-A 738 259 |
| I.5C-6 | CH$_3$ | 4-Cl—C$_6$H$_4$ | CH$_2$CH$_3$ | EP-A 738 259 |

TABLE 1.6A

Compounds of the formula IA where Q is phenyl, R' is —C(COCH$_3$)=NOCH$_3$, n is 0, R" is (het)aryloxymethylene with or without substitution, where the (het)aryl group with or without substitution has the following meanings:

| No. | (Het)aryl with or without substitution | Literature |
|---|---|---|
| I.6A-1 | 2-CH$_3$—C$_6$H$_4$ | EP-A 498 188 |
| I.6A-2 | 2,5-(CH$_3$)$_2$—C$_6$H$_3$ | EP-A 498 188 |
| I.6A-3 | 2,4-(CH$_3$)$_2$—C$_6$H$_3$ | EP-A 498 188 |
| I.6A-4 | 2,3,5-(CH$_3$)$_3$—C$_6$H$_2$ | EP-A 498 188 |
| I.6A-5 | 2-CH$_3$, 4-C[CH$_3$]=NOCH$_3$—C$_6$H$_3$ | EP-A 498 188 |

TABLE 1.6B

Compounds of the formula IA where Q is phenyl, R' is —C(COCH$_3$)=NOCH$_3$, n is 0, R" is (het)aryloxy with or without substitution, where the (het)aryl group with or without substitution has the following meanings:

| No. | (Het)aryl with or without substitution | Literature |
|---|---|---|
| I.6B-1 | C$_6$H$_5$ | EP-A 498 188 |
| I.6B-2 | 6-[2-CN—C$_6$H$_4$—O]-pyrimidin-4-yl | EP-A 498 188 |

TABLE 1.7A

Compounds of the formula IA where Q is phenyl, R' is —C(COCH$_2$CH$_3$)=NOCH$_3$, n is 0, R" is (het)aryloxymethylene with or without substitution, where the (het)aryl group with or without substitution has the following meanings:

| No. | (Het)aryl with or without substitution | Literature |
|---|---|---|
| I.7A-1 | 2-CH$_3$—C$_6$H$_4$ | EP-A 498 188 |
| I.7A-2 | 2,5-(CH$_3$)$_2$—C$_6$H$_3$ | EP-A 498 188 |
| I.7A-3 | 2,4-(CH$_3$)$_2$—C$_6$H$_3$ | EP-A 498 188 |
| I.7A-4 | 2,3,5-(CH$_3$)$_3$—C$_6$H$_2$ | EP-A 498 188 |
| I.7A-5 | 2-CH$_3$, 4-Cl[CH$_3$]=NOCH$_3$—C$_6$H$_3$ | EP-A 498 188 |

TABLE 1.7B

Compounds of the formula IA where Q is phenyl, R' is —C(COCH$_2$CH$_3$)=NOCH$_3$, n is 0, R" is (het)aryloxy with or without substitution, where the (het)aryl group with or without substitution has the following meanings:

| No. | (Het)aryl with or without substitution | Literature |
|---|---|---|
| I.7B-1 | C$_6$H$_5$ | EP-A 498 188 |
| I.7B-2 | 6-[2-CN—C$_6$H$_4$—O]-pyrimidin-4-yl | EP-A 498 188 |

TABLE 1.8A

Compounds of the formula IA where Q is phenyl, R' is —N(OCH$_3$)—CO$_2$CH$_3$, n is 0, R" is (het)aryloxymethylene with or without substitution, where the (het)aryl group with or without substitution has the following meanings:

| No. | (Het)aryl with or without substitution | Literature |
|---|---|---|
| I.8A-1 | 2-CH$_3$—C$_6$H$_4$ | WO-A 93/15,046 |
| I.8A-2 | 2,5-(CH$_3$)$_2$—C$_6$H$_3$ | WO-A 93/15,046 |
| I.8A-3 | 2,4-(CH$_3$)$_2$—C$_6$H$_3$ | WO-A 93/15,046 |
| I.8A-4 | 2,3,5-(CH$_3$)$_3$—C$_6$H$_2$ | WO-A 93/15,046 |
| I.8A-5 | 2-Cl, 5-CH$_3$—C$_6$H$_3$ | WO-A 93/15,046 |
| I.8A-6 | 2-CH$_3$, 4-C[CH$_3$]=NOCH$_3$—C$_6$H$_3$ | WO-A 93/15,046 |
| I.8A-7 | 2-CH$_3$, 4-C[CH$_3$]=NOCH$_2$CH$_3$—C$_6$H$_3$ | WO-A 93/15,046 |
| I.8A-8 | 2-CH$_3$, 4-C[CH$_2$CH$_3$]=NOCH$_3$—C$_6$H$_3$ | WO-A 93/15,046 |
| I.8A-9 | 2-CH$_3$, 4-C[CH$_2$CH$_3$]=NOCH$_2$CH$_3$—C$_6$H$_3$ | WO-A 93/15,046 |
| I.8A-10 | 1-[4-Cl—C$_6$H$_4$]-pyrazol-3-yl | WO-A 96/01256 |

TABLE 1.8B

Compounds of the formula IA where Q is phenyl, R' is —N(OCH$_3$)—CO$_2$CH$_3$, n is 0, R" is CH$_2$ON = CR$^\alpha$R$^\beta$, where R$^\alpha$ and R$^\beta$ have the following meaning:

| No. | R$^\alpha$ | R$^\beta$ | Literature |
|---|---|---|---|
| I.8B-1 | CH$_3$ | 3,5-Cl$_2$—C$_6$H$_3$ | WO-A 93/15,046 |

It can be assumed that the method according to the invention can be employed in principle in all crop plants and horticulturally useful plants having a modified pathogen resistance against harmful fungi. Examples of such plants are bananas, coffee, potatoes, rape seed, turnips, asparagus, tea, tomatoes, onion species, and gramineae such as barley, oats, maize, rice, rye and wheat; the effect is particularly pronounced in potatoes, turnips, asparagus, onion species and gramineae, and the method according to the invention is particularly recommended for use in gramineae, for example in wheat, barley and rice. Methods for increasing the pathogen resistance of such crop plants are well known to a person skilled in the art and described in the literature, for example in WO-A 95/05467, WO-A 94/8009 and the publications J. Lamb et al., Biotechnology 10 (1992), 1436–1445, H. Anzai et al., Mol. Gen. Genet. 219 (1989), 492–494, R. Grison et al., Nature Biotechnology 14 (1996), 643–646, H. Uchimiya et al., Biotechnology 11 (1993), 835–837, G. Jach et al., Biopractice 1 (1992), 33–40, J. Logemann et al, Biotechnology 10 (1992), 305–308 and G. Strittmatter et al., Biotechnology 13 (1995), 1085–1089.

Depending on the kind of crop plant, the application rates of compounds IA or IB are from 0.5 to 0.01 kg/ha, preferably 0.3 to 0.01 kg/ha, in particular 0.15 to 0.05 kg/ha.

For the method according to the invention, the compounds I can be formulated and applied in a manner customary for use in crop protection (cf. literature cited at the outset).

The method according to the invention has the advantage, among others, that a large number of harmful fungi can be controlled successfully with just one active compound of the formula I; according to the prior art, this would have required a plurality of fungicidally active compounds which may in certain cases have had adverse interactions.

In some instances, the application rates of the active compounds of the formula I could be considerably reduced as compared to the customary application rates, without adversely affecting the activity. This result is surprising. In the case of kresoxim-methyl (methyl methoxyimino-α-(o-tolyloxy)-o-tolylacetate), for example, application rates of below 0.05 kg/ha, in particular from 0.04 to 0.01 kg/ha, are sufficient.

The method according to the invention can be employed particularly advantageously in crop plants which have an increased pathogen resistance to those harmful fungi which in general cannot be controlled completely with the individual active compounds of the formula I. Thus, it is possible to improve the usually insufficient activity of azoxystrobin (methyl(E)-2-(2-[6-(2-cyanophenoxy)pyrimidin-4-yloxy]phenyl)-3-methoxyacrylate) against cereal mildew in mildew-resistant barley or wheat varieties disproportionally.

The method according to the invention can also be employed successfully in crop plants having an increased pathogen resistance to those harmful fungi which can be effectively controlled with active compounds of the formula I. Here, it is often possible to reduce the required application rate considerably.

For example, less of the active compound kresoxim-methyl is required to render entirely free of infection those varieties of crop plants such as wheat, barley, grapevines or apple trees which have increased resistance to powdery mildew species, compared to the higher application rates of active strobilurin ingredient which are required to render nonresistant plants mildew-free. Comparative experiments show clearly that in the barley varieties A HOR 1528/9, A HOR 2978/80, A HOR 3141/78 and A HOR 15 5458/70, which have increased mildew resistance, considerably lower amounts of kresoxim-methyl allow the same control of barley mildew as in the common, commercially available varieties "Asse" and "Sonja" which do not have any increased mildew resistance.

The same applies to resistant and nonresistant grapevines and their treatment with kresoxim-methyl for controlling Plasmopara viticola.

This applies correspondingly to the active compound azoxystrobin for the control of a large number of different phytopathogenic fungi in resistant and nonresistant crop plants. Examples of economically important phytopathogenic fungi include the following pathogen/host pairs from the class of the idiomcetes: Puccinia species in cereals and lawns, Rhizoctonia species in cotton, rice and lawns, *Hemileia vastatrix* in coffee, Ustilago species in cereals and sugar cane; from the group of the Ascomycetes Erysiphe species in wheat, barley and rye, Erysiphe and Sphaerotheca species in curcurbits, *Podosphaera leucotricha* in apples, Uncinula necator in grapevines, Venturia species in apples and pears; from the class of the *Deuteromycetes Botrytis cinerea* in strawberries, grapevines, vegetables and ornamentals, Alternaria species in vegetables and fruit, *Pyricularia oryzae* in rice and lawns, *Cercospora arachidicola* in groundnuts, *Pseudocercosporella herpotichoides* in wheat and barley, Helminthosporium species in cereals, Septoria species in cereals and vegetables; and from the class of the *Phycomycetes Phytophthora* infestans in tomatoes and potatoes, *Plasmopara viticola* in grapevines and Pseudoperonospora species in hops and vegetables.

COMPARATIVE EXPERIMENT

Activity against powdery mildew of barley (*Exysiphe graminis* f. sp. *hordei*)

Leaves of potted barley seedlings of the various varieties were sprayed to runoff point with an aqueous active compound formulation prepared from a stock solution comprising 10% of active compound (kresoxim-methyl), 63% of cyclohexanone and 27% of emusifier. The next day, the leaves were dusted with spores of powdery mildew of barley (*Erysiphe graminis* f. sp. *hordei*). The test plants were subsequently kept in a greenhouse at 20°–22° C. and 75–80% relative atmospheric humidity. 6 days after the inoculation, the extent of mildew development was determined visually as % infection of the total leaf area treated.

Barley variety % infection of the leaves after application of aqueous kresoxim-methyl formulation, kresoxim-methyl content in ppm

|  | 2 ppm | 1 ppm | 0.5 ppm | 0.25 ppm | Untreated |
|---|---|---|---|---|---|
| "Asse" commercially available variety | 7 | 80 | 100 | 100 | 100 |
| "Sonja" commercially available variety | 5 | 70 | 100 | 100 | 100 |

Varieties having increased resistance to mildew

| A HOR 1528/91 | 0 | 7 | 30 | 90 | 100 |
|---|---|---|---|---|---|
| A HOR 2978/80 | 2 | 15 | 40 | 90 | 100 |
| A HOR 3141/78 | 1 | 10 | 70 | 100 | 100 |
| A HOR 5458/70 | 0 | 2 | 40 | 90 | 100 |

The barley seedlings (*Hordeum vulgaris*) of the varieties used in the comparative experiment can be obtained from: Institut für Pflanzengenetik und Kulturpflanzenforschung Gatersleben, Genbank, Corrensstr. 3, 06466 Gatersleben, Germany.

We claim:

1. A method for controlling harmful fungi in crop plants, wherein the crop plants have a moitied pathogen resistance to said harmful fungi and wherein said harmful fungi belong to a class selected from the group consisting of Basidiomycetes, Ascomycetes, Deuteromycetes and Phycomycetes, which comprises treating the plants with an effective amount of active compound of formula IA or IB

IA

IB where ... is a single or double bond and where:

$R'$ is $-C[CO_2CH_3]=CHOCH_3$, $-C[CO_2CH_3]=NOCH_3$, $-C[CONHCH_3]=NOCH_3$, $-[CO_2CH_3]=CHCH_3$, $-C[CO_2CH_3]=CHCH_2CH_3$, $-C[COCH_3]=NOCH_3$, $-C[COCH_2CH_3]=NOCB_3$, $-N(OCH_3)-CO_2CH_3$, $-N(CH_3)-CO_2CH_3$, $-N(CH_2CH_3)-CO_2CH_3$, $R''$ is a C-organic radical which is attached directly or via an oxy, mercapto, amino or alkylamino group, or together with a group X and the ring Q or T to which they are attached forms a bicyclic, partially or fully unsaturated system with or without substitution which may, in addition to carbon ring members, contain hetero atoms from the group consisting of oxygen, sulfur and nitrogen, $R^x$ is $-OC[CO_2CH_3]=CHOCH_3$, $-OC[CO_2CH_3]=CHCH_3$, $-OC[CO_2CH_3]=CHCH_2CH_3$, $-SC$

[CO₂CH₃]=CHOCH₃, —SC[CO₂CH₃]=CHCH₃, —SC[CO₂CH₃]=CHCH₂CH₃, —N(CH₃)C[CO₂CH₃]=CHOCH₃, —N(CH₃)C[CO₂CH₃]=NOCH₃, —CH₂C[CO₂CH₃]=CHOCH₃, —CH₂C[CO₂CH₃]=NOCH₃, —CH₂C[CONCH₃]=NOCH₃,

R<sup>y</sup> is oxygen, sulfur, =CH— or =N—, n is 0, 1, 2 or 3, where the radicals X may be different if n>1;

X is cyano, nitro, halogen, C₁–C₄-alkyl, C₁–C₄-haloalkyl, C₁–C₄-alkoxy, C₁–C₄-haloalkozy, C₁–C₄-alkylthio or, if n>1a C₃–C₅-alkylene, C₃–C₅-alkenylene, oxy-C₂–C₄-alkylene, oxy-C₁–C₃-alkylenoxy, oxy-C₂–C₄-alkenylene, oxy-C₂–C₄-alkenylenoxy or butadienediyl group which is attached to two adjacent carbon atoms of the phenyl ring, where these chains in turn may carry one to three of the following radicals: halogen, C₁–C₄-alkyl, C₁–C₄-haloalkyl, C₁–C₄-alkoxy, C₁–C₄-haloalkozy or C₁–C₄-alkylthio, Y is =C— or —N—, Q is phenyl, pyrrolyl, thienyl, furyl, pyrazolyl, inidazolyl, oxazolyl, isoxazolyl, thiazolyl, thiadiazolyl, triazolyl, pyridinyl, 2-pyridonyl, pyrimidinyl and triazinyl, T is phenyl, oxazolyl, thiazolyl, thiadiazolyl, oxadiazolyl, pyridinyl, pyrimidinyl and triazinyl.

2. A method as claimed in claim 1, wherein the crop plants are treated with from 0.5 to 0.01 kg/ha of a compound of the formula IA or IB.

3. The method of claim 1 wherein the the active compound is of formula IA wherein Q denotes phenyl and wherein R' is —C(CO₂CH₃)=CHOCH₃, and R" is selected from the group consisting of 2-methylphenoxyme-thylene, 2,5-dimethylphenoxymethylene, 2-methyl-4-(1-methoxyimino)ethylphenoxymethylene, 2-propyl-6-trifluoromethylpyrimidin-4-yloxymethylene, 2,4-dimethylphenoxymethylene, phenoxy, 6-(2-cyanophenoxy)pyrimidin-4-yloxy, 2-(1-(2,4-dichlorophenyl)-5-trifluoromethylpyrazol-4-yl)ethylene, 2-(1-(4-chlorophenyl)pyrazol-4-yl)ethylene, 2-(2-trifluoromethylphenyl)ethylene, 2-(3-chlorophenyl)ethylene, 2-(4-biphenyl)ethylene, a group CH₂ON=C(CH₃)R<sup>β</sup> and a group CH₂ON=C(CH₃)CR<sup>δ</sup>=NOR<sup>ε</sup>, wherein R<sup>β</sup> is 4-chlorophenyl, 3-trifluoromethylphenyl or 4-ethoxypyrimidin-2-yl;

R<sup>δ</sup> is methyl, phenyl or 4-chlorophenyl; and

R<sup>ε</sup> is methyl or ethyl; or

R' is —C(CO₂CH₃)=NOCH₃, and

R" is selected from the group consisting of 2-methylphenoxymethylene, 2,5-dimethylphenoxymethylene, 2,4-dimethylphenoxymethylene, 2,3,5-trimethylphenoxymethylene, 2-chloro-5-methylphenoxymethylene, 2-methyl-4-(1-methoxyimino)ethylphenoxymethylene, phenoxy, 6-(2-cyanophenoxy)pyrimidin-4-yloxy, a group CH₂ON=C(CH₃)R<sup>β</sup> and a group CH₂ON=C(CH₃)CR<sup>δ</sup>=NOR<sup>ε</sup>, wherein R<sup>β</sup> is 4-chlorophenyl, 3-chlorophanyl, 4-trifluoromethylphenyl, 3-trifluoromethylphenyl, 4-ethoxypyrimidin-2-yl or 3,5-dichlorophenyl;

R<sup>δ</sup> is methyl, phenyl or 4-chlorophenyl; and

R<sup>ε</sup> is methyl or ethyl; or

R' is —C(CONHCH₃)=NOCH₃, and

R" is selected from the group consisting of 2-methylphenoxymethylene, 2,5-dimethylphenoxymethylene, 2,4-dimethylphenoxymethylene, 2,3,5-trimethylphenozymethylene, 2-methyl-4-(1-methoxyimino)ethylphenoxymethylene, 1-(4-chlorophenyl)pyrazol-3-yloxymethylene, 1-(2,4-dichlorophenyl)pyrazol-3-yloxymethylene, phenoxy, 6-(2-cyanophenoxy)pyrimidin-4-yloxy, a group CH₂ON=C(CH₃)R<sup>β</sup> and a group CH₂ON=C(CH₃)CR<sup>δ</sup>=NOR<sup>ε</sup>, wherein R<sup>β</sup> is 4-chlorophenyl, 3-chlorophenyl, 4-trifluoromethylphenyl, 3-trifluoromethylphenyl, 3,5-dichlorophenyl or 4-ethoxypyrimidin-2-yl;

R<sup>δ</sup> is methyl, phenyl or 4-chlorophenyl; and

R<sup>ε</sup> is methyl or ethyl; or

R<sup>δ</sup> is 4-fluorophenyl and R<sup>ε</sup> is mothyl; or

R' is —C(CO₂CH₃)=CHCH₃, and

R" is selected rrom the group consisting of 2-methylphenoxymethylene, 2,5-dimethylphenoxymethylene, 2,4-dimethylphenoxymethylene, 2,3,5-trimethylphenoxymethylene, 2-chloro-5-methylphenoxymethylene, 2-methyl-4-(1-methoxyimino)ethylphenoxymethylene, 1-(4-chlorophenyl)pyrazol-3-yloxymethylene, phenoxy and a group CH₂ON=C(CH₃)CR<sup>δ</sup>=NOR<sup>ε</sup>, wherein R<sup>δ</sup> is methyl, phenyl or 4-chlorophenyl; and R<sup>ε</sup> is methyl or ethyl; or R' is —C(CO₂CH₃)=CHCH₂CH₃, and R" is selected from the group consisting of 2-methylphenoxymethylene, 2,5-dimethylphenoxymethylene, 2,4-dibmethylhenoxymethylene, 2,3,5-trimethylphanoxymethylens, 2-chloro-5-methylphanoxymethylene, 2-methyl-4-(1-methoxyimino)ethylphenoxymethylene, phenoxy and a group CH₂ON=C(CH₃)CR<sup>δ</sup>=NOR<sup>ε</sup>, wherein R<sup>δ</sup> is methyl, phenyl or 4-chlorophenyl; and R<sup>ε</sup> is methyl or ethyl; or R' is —C(COCH₃)=NOCH₃ or —C(COCH₂CH₃)=NOCH₃, and R" is selected from the group consisting of 2-methylphenoxymethylene, 2,5-dimethylphethylene, 2,4-dimethylphenoxymethylene, 2,3,5-trimethylphenozymethylene, 2-methyl-4-(1-methoxyimino)ethylphenoxymethylene, phenoxy and 6-(2-cyanophenoxy)pyrimidin-4-yloxy, or R' is —N(OCH₃)—CO₂CH₃, and R" is selected from the group consisting of 2-methylphenoxymethyleno, 2,5-dimethylphenoxymethylene, 2,4-dimethylphenoxymethylene, 2,3,5-dimethylhenoxymethylene, 2,3,5-trimethylphenoxymethylene, 2-chloro-5-methylphenoxymethylene, 2-methyl-4-(1-methoxyimino)ethylphenoxymethylene, 2-methyl-4-(1-methoxyimino)propylphenoxymethylene, 2-methyl-4-(1-methoxyimino)propylphenoxymethylene, 1-(4-chlorophenyl)pyrazol-3-yloxymethyl and CH₂ON=C(CH₃)(3,5-dichlorophenyl).

4. The method of claim 1 wherein the active compound is selected from the group consisting of compounds I.1B-2, I.2A-1, I.2C-4, I.3A-2, I.3B-1 and I.8A-10, having the following formulae:

(I.1B-2)
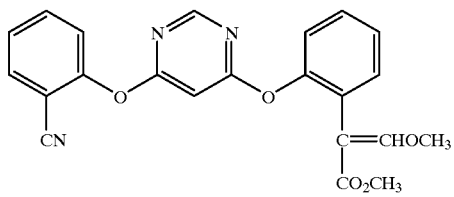

(I.2A-1)
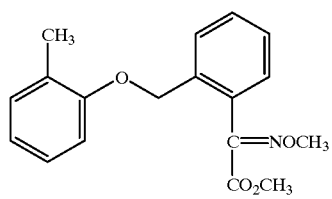

(I.2C-4)
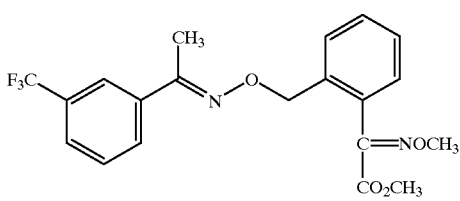

(I.3A-2)
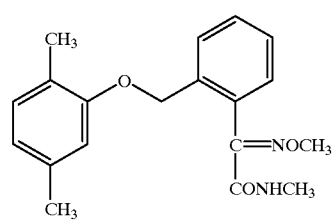

(I.3B-1)
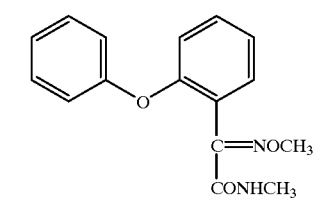

(I.8A-10)
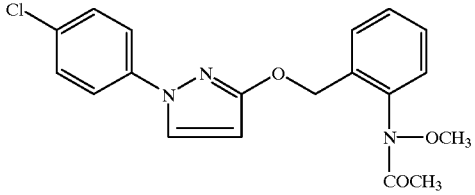

5. The method of claim 1 wherein the crop plants have an increased pathogen resistance to harmful fungi.

6. The method of claim 5 wherein the crop plants are selected from the group consisting of bananas, coffee, potatoes, rape seed, turnips, asparagus, tea, tomatoes, onion species and granineae.

7. The method of claim 5 wherein the crop plants are selected from the group consisting of barley, oats, maize, rice, rye and wheat.

8. The method of claim 5 wherein the crop plants are selected from the group consisting of barley, rice and wheat.

9. The method of claim 5 wherein the active compound is methyl methoxyimino-α-(o-tolyloxy)-o-tolylacetate.

10. The method of claim 9 wherein the active compound is applied in an amount of less than 0.05 kg/ha.

11. The method of claim 10 wherein the active compound is applied in an amount of from 0.04 to 0.01 kg/ha.

12. The method of claim 9, wherein the crop plants are grapevines.

13. The method of claim 12, wherein the pathogen is Plasmopara viticola.

14. The method of claim 5 wherein the active compound is methyl (E)-2-{2-[6-(2-cyanophenozy)pyrimidin-4-yloxyl]phenyl}-3-methoxyacrylate.

15. The method of claim 14 wherein the pathogen is cereal mildew.

16. The method of claim 14 wherein the crop plant is mildew-resistant barley or wheat.

17. The method of claim 1, wherein the harmful fungi are selected from the group consisting of Puccinia species, Rhizoctonia species, *Hemilaia vastatrix*, Ustilago species, Erysiphe species, Sphaerotheca species, *Podosphaera leucotricha*, Uncinula necator, Venturia species, Botrytis cinerea, Alternaria species, *Pyricularia oryzae, Cercospora arachidicola, Pseudocercosporella herpotichoides*, Helminthosporium species, Septoria species, Phytophthora infestans, *Plasmopara viticola* and Pseudoperonospora species.

* * * * *

UNITED STATES PATENT AND TRADEMARK OFFICE
CERTIFICATE OF CORRECTION

PATENT NO. : 6,221,808 B1
DATED : April 24, 2001
INVENTOR(S) : Schmidt et al.

It is certified that error appears in the above-identified patent and that said Letters Patent is hereby corrected as shown below:

Column 12, claim 1,
Line 32, "moitied" should be -- modified --.
Line 53, "-[Co$_2$CH$_3$]" should be -- -C[CO$_2$CH$_3$] --.

Column 13, claim 1,
Line 5, "-CH$_2$C[CONCH$_3$]=CHOCH$_3$" should be -- -CH$_2$C[CONHCH$_3$]=CHOCH$_3$ --.
Line 11, "n>1a" should be -- n > 1, a --.
Line 21, "inidazolyl" should be -- imidazolyl --.

Column 13, claim 2,
Line 26, "A method as claimed in" should be -- The method of --.

Column 13, claim 3,
Line 29, "the the" should be -- the --.
Line 62, "3-chlorophanyl" should be -- 3-chlorophenyl --.

Column 14, claim 3,
Lines 5, "trimethylphenozymethylene" should be -- trimethylphenoxymethylene --.
Line 18, "mothyl" should be -- methyl --.
Line 36, "dibmethylhenoxymethylene" should be -- dimethylphenoxymethlene --.
Line 37, "trimethylphanoxymethylens" should be -- trimethylphenoxymethylene --.
Line 38, "methylphanoxymethylene" should be -- methylphenoxymethylene --.
Line 47, "2,5-dimethylphethylene" should be -- 2,5-dimethylphenoxymethylene --.
Line 49, "trimethylphenozymethylene" should be -- trimethylphenoxymethylene --.
Line 54, "2-methylphenoxymethyleno" should be -- 2-methylphenoxymethylene --.
Line 56, "dimethylhenoxymethylene" should be -- dimethylphenoxymethylene --.
Line 61, "4-(1-methoxyimino)" should be -- 4-(1-ethyoxyimino) --.

UNITED STATES PATENT AND TRADEMARK OFFICE
CERTIFICATE OF CORRECTION

PATENT NO. : 6,221,808 B1
DATED : April 24, 2001
INVENTOR(S) : Schmidt et al.

It is certified that error appears in the above-identified patent and that said Letters Patent is hereby corrected as shown below:

<u>Column 16, claim 14,</u>
Lines 32 and 33, "(E)-2-{2-[6-(2-cyanophenozy)pyrimidin-4-yloxyl]phenyl}-3-methoxyacrylate" should be -- (E)-2-{2-[6-(2-cyanophenoxy)pyrimidin-4-yloxy]phenyl}-3-methoxyacrylate --.

<u>Column 16, cliam 17,</u>
Line 39, "*Hemilaia*" should be -- *Hemileia* --.

Signed and Sealed this

Eighteenth Day of December, 2001

*Attest:*

*Attesting Officer*

JAMES E. ROGAN
*Director of the United States Patent and Trademark Office*